US008645155B2

(12) United States Patent
Menon et al.

(10) Patent No.: US 8,645,155 B2
(45) Date of Patent: Feb. 4, 2014

(54) AUTOMATIC LOADING OF MEDICAL DATA IN INTEGRATED INFORMATION SYSTEM (75) Inventors: Manoj K Menon, Adwaitham (IN); Aavishkar Bharara, Rohini (IN)

(73) Assignee: General Electric Company, Schenectady, NY (US)

(*) Notice: Subject to any disclaimer, the term of this patent is extended or adjusted under 35 U.S.C. 154(b) by 1568 days.

(21) Appl. No.: 11/465,660

(22) Filed: Aug. 18, 2006

(65) Prior Publication Data
US 2008/0046288 A1   Feb. 21, 2008

(51) Int. Cl.
G06Q 50/00   (2012.01)
G06Q 10/00   (2012.01)

(52) U.S. Cl.
USPC .................................. 705/2; 705/3

(58) Field of Classification Search
USPC ........................................................ 705/2
See application file for complete search history.

(56) References Cited

U.S. PATENT DOCUMENTS

| | | | |
|---|---|---|---|
| 5,781,442 A * | 7/1998 | Engleson et al. | 700/214 |
| 7,072,840 B1 * | 7/2006 | Mayaud | 705/2 |
| 2002/0082866 A1 * | 6/2002 | Ladouceur et al. | 705/2 |
| 2003/0052788 A1 | 3/2003 | Kwong-Tai | |
| 2003/0074223 A1 * | 4/2003 | Hickle et al. | 705/2 |
| 2003/0135388 A1 * | 7/2003 | Martucci et al. | 705/2 |
| 2004/0249419 A1 | 12/2004 | Chapman | |
| 2005/0012617 A1 | 1/2005 | DiSilvestro | |
| 2005/0149358 A1 | 7/2005 | Sacco | |
| 2005/0240441 A1 | 10/2005 | Suzuki | |

OTHER PUBLICATIONS

Paquet, Description of shape information for 2-D and 3-D objects, Signal Processing: Image Communication, vol. 16, Issues 1-2, Sep. 2000, pp. 103-122, ISSN 0923-5965.*
http://www.surgichip.com/index.htm (Surgichip homepage attached).

* cited by examiner

*Primary Examiner* — Tran Nguyen
(74) *Attorney, Agent, or Firm* — Hanley, Flight and Zimmerman, LLC (57) ABSTRACT

A method of automatic loading of medical data in an integrated information system is disclosed herein. The method comprises steps of triggering a data acquisition unit to acquire medical data from at least one medical information system, acquiring the medical data from the medical information system, and displaying the medical data in a video display unit in a selected format. Also disclosed is an integrated information system configured for automatic loading of medical data. The integrated information system comprises a medical workstation and at least one medical information system coupled to the medical workstation. The medical workstation is configured for automatic loading of the medical data concerning a medical object from the medical information system.

23 Claims, 5 Drawing Sheets

AUTOMATIC LOADING OF MEDICAL DATA IN INTEGRATED INFORMATION SYSTEM

FIELD OF INVENTION

The invention relates generally to an integrated information system and more particularly to automatic loading of medical data in the integrated information system.

BACKGROUND OF THE INVENTION

Medical errors are the eighth-leading cause of death in the United States. Deaths from medical errors occur at a rate greater than deaths from motor vehicle accidents, breast cancer or AIDS. A report from the National Academy of Sciences Institute of Medicine cited studies showing that thousands of people die each year because of the medical errors. The medical errors account for a huge loss in terms of time and money.

The cause of a large number of medical errors can generally be attributed to a manual or partially automated process employed in a medical facility for loading a medical data concerning a medical object. Considering an existing workflow in a hospital, loading of the medical data is often a manual process. One of the methods for a surgeon to get information about a scheduled medical procedure is by enquiring the medical object in person. Alternatively, a medical image of the medical object concerning the medical procedure may be displayed on, for example, a light box.

In a workflow where a partially automated process is involved, a unique identifier is associated with the medical object upon scheduling the medical procedure. The unique identifier comprises one or more identification details of the medical object. Further, the medical image of the medical object is displayed in a mobile cart.

The primary limitation in the conventional process involved in procuring and loading the medical data, is a possible occurrence of a medical error. For example, the medical error can involve a wrong selection of the medical object or a mix up of the medical data of one medical object with the medical data of another medical object. The wrong selection of the medical object can lead to a wrong medical procedure being administered on the medical object. The mix up in the medical data can lead to critical medical errors such as operating on the left knee instead of the right knee, or operating on the brain instead of on the abdomen.

Hence there exists a need for providing a system and method for ensuring a match between the medical data and the medical object while loading the medical data concerning the medical object, in order to avoid medical errors.

SUMMARY OF THE INVENTION

The above-mentioned shortcomings, disadvantages and problems are addressed herein which will be understood by reading and understanding the following specification.

In an embodiment, the invention provides a method of automatic loading of medical data in an integrated information system. The method comprises steps of triggering a data acquisition unit to acquire medical data from at least one medical information system, acquiring the medical data from the medical information system and displaying the medical data in a video display unit in a selected format. The selected format is a selection and arrangement of the medical data in a format specified by a medical staff.

In another embodiment of the invention, an integrated information system configured for automatic loading of medical data is provided. The integrated information system comprises a medical workstation and at least one medical information system coupled to the medical workstation. The medical information systems work together in a synchronized mode with the medical workstation. The medical workstation is configured for automatic loading of the medical data concerning a medical object.

In yet another embodiment of the invention, a computer program product stored in a computer readable media for automatic loading of medical data in an integrated information system is provided. The computer program product comprises a routine for triggering a data acquisition unit to acquire the medical data from at least one medical information system, a routine for acquiring the medical data from the medical information system and a routine for displaying the medical data in a video display unit in a selected format.

Systems and methods of varying scope are described herein. In addition to the aspects and advantages described in the summary, further aspects and advantages will become apparent by reference to the drawings and with reference to the detailed description that follows.

DETAILED DESCRIPTION OF THE INVENTION

In the following detailed description, reference is made to the accompanying drawings that form a part thereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

In various embodiments of the invention, an integrated information system and a method of automatic loading of medical data in the integrated information system are described. However, the embodiments are not limited and may be implemented in connection with different applications. Embodiments of the invention can be adapted in networked environments. The design can be carried further and implemented in various forms and specifications.

The invention provides a method and system for automatic loading of medical data concerning a medical object thereby avoiding medical errors associated wit a manual procedure. The medical object refers to an article, object, person or animal. Examples include, but are not limited to, packages, parcels, containers, medications, medical devices, instruments, implements, containers and the like in a medical or hospital environment.

The medical data comprises an object data and at least one of a diagnostic data and a drug data. One skilled in the art shall however appreciate that the examples of the medical data are not limited to the examples given above and the invention shall have full scope of the claims. The object data comprises general information concerning the medical object such as identity, age, height, weight, sex, race, family and genetic medical data, medical history, physical handicaps, known medical conditions, known medical allergies, and current ailment conditions such as symptoms, duration, temperature, blood pressure, pulse rate, blood test data, urine test data, physician observations and the like.

The drug data can comprise prescriptions, allergy information, drug interaction information, drug treatment information and overdose information. The diagnostic data concerning the medical object includes but not limited to radiology information, laboratory information and clinical information concerning the medical object. The radiology information can comprise at least one medical image of the medical object. The medical image of the medical object can be obtained from an imaging device such as but not limited to an ultrasound system, a computed tomography system, a magnetic resonance imaging system and an X ray system.

Figure 1:
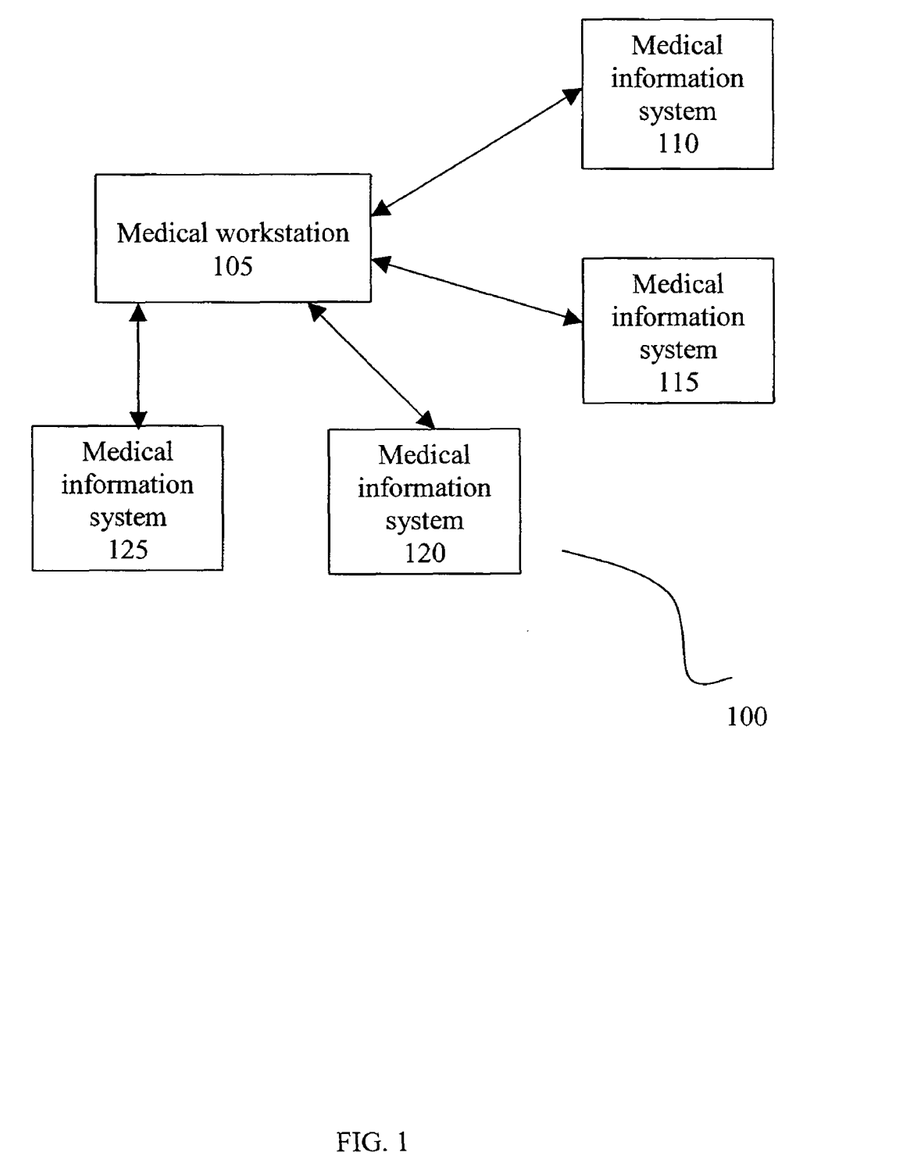
FIG. 1 shows a block diagram of an integrated information system, in an embodiment of the invention.

In an embodiment, the invention provides an integrated information system 100 configured for automatic loading of medical data concerning a medical object as shown by FIG. 1. The integrated information system 100 configured for acquisition and processing of the medical data concerning the medical object, can be installed in a medical facility such as a hospital or clinic for recording the medical data within the hospital or clinic and performing an integrated central management of the medical data.

The integrated information system 100 can comprise a medical workstation 105 and a plurality of subsystems, such as medical information systems 110, 115, 120 and 125. The medical information system 110 includes any of a laboratory information system (LIS), a clinical information system (CIS), a radiology information system (RIS), a picture archival and communication system (PACS), or other system for handling medical information. As known in the art, PACS enables an electronic acquiring, storing and transmission of the medical images. One skilled in the art shall however appreciate that the examples of the medical information systems are not limited to the examples given above and the invention shall have full scope of the claims.

In one embodiment, each of the medical information systems 110, 115, 120 and 125 is capable of communicating with the medical workstation 105 by way of a wire-line Local Area Network (LAN). The medical workstation 105 is in turn connected with a server though the LAN for performing a control and processing of the medical data. In other embodiments, there may be more or less than four medical information systems 110, 115, 120 and 125 coupled to medical workstation 105 by the same or different communication interfaces.

Figure 2:
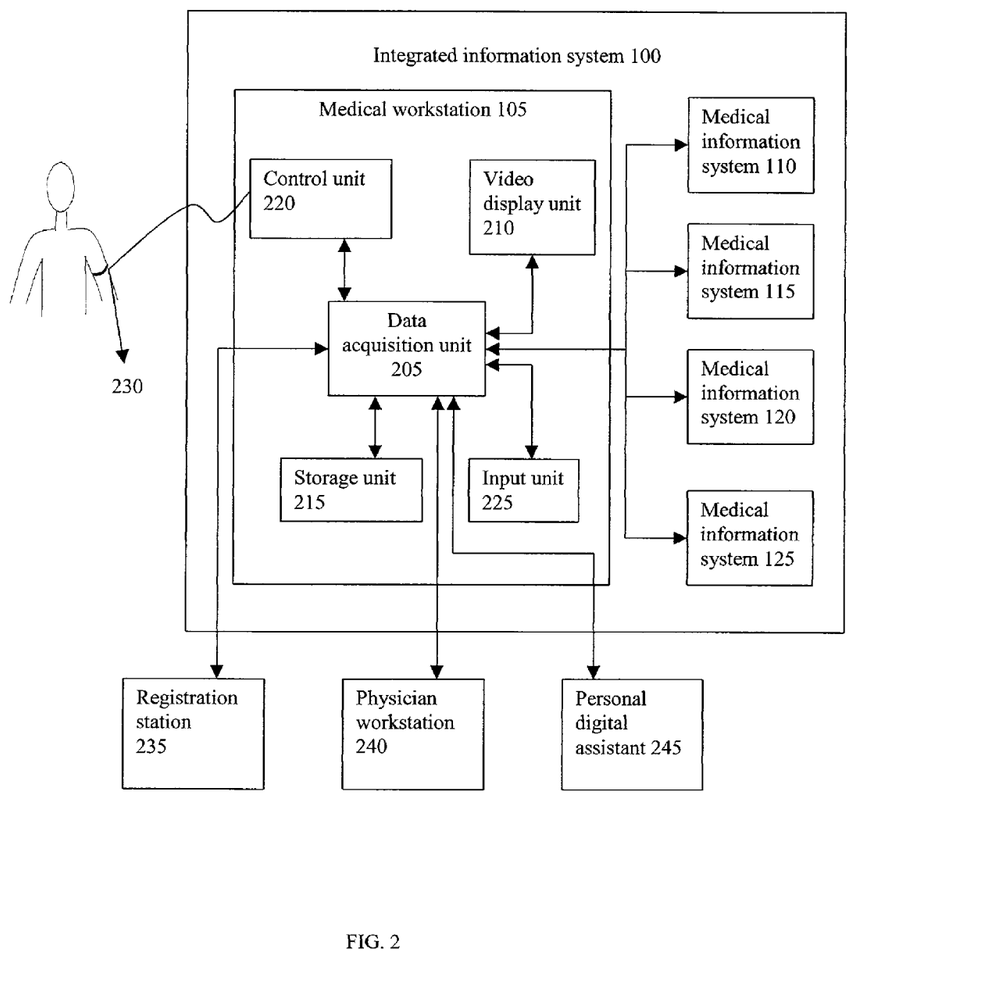
FIG. 2 shows a block diagram of an integrated information system, in another embodiment of the invention.

FIG. 2 shows a block diagram of the integrated information system 100, in another embodiment of the invention. The medical workstation 105 comprises a data acquisition unit 205 and a video display unit 210 coupled to the data acquisition unit 205. The data acquisition unit 205 controls an overall operation of the medical workstation 105. The data acquisition unit 205 is configured to acquire medical data from one or more medical information systems 110, 115, 120 and 125 coupled to the medical workstation 105. In various embodiments, the data acquisition unit 205 communicates with the medical information systems 110, 115, 120 and 125 using a healthcare data standard. In one specific embodiment, the data acquisition unit 205 communicates with the medical information system such as PACS using the DICOM standard and with other medical information systems such as LIS, RIS and CIS using the HL7 standard.

The video display unit 210 coupled to the data acquisition unit 205 comprises a video or a computer monitor, a Liquid Crystal Display (LCD) display, a cathode ray tube display, a dot-matrix display, a touch screen display, a laser activated display or any other display providing a convenient display of the medical data. The video display unit 210 may also include an annunciator, loudspeaker, or other sound transducer for providing audible information that can be perceived by a person, such as an alarm, a reminder or a warning, e.g., via pre-recorded and/or synthesized speech.

The video display unit 210 can be configured to display the medical data in a selected format. The selected format is a selection and arrangement of the medical data in a format specified by a medical staff such as a surgeon or other healthcare worker. The selected format is generally related to the medical procedure to be performed on the medical object. In the absence of the selected format a default format can be employed for the display.

In another embodiment of the invention, the medical workstation 105 can comprise a hardware configuration, in which multiple components are interconnected by a bus so as to be enabled for mutual data exchanges under the control of the data acquisition unit 205. The components comprise a wireless LAN card (not shown), a control unit 220, a storage unit 215 and an input unit 225. The wireless LAN card (not shown) enables communication with the server for communicating the medical data by way of access points installed in multiple corners of the hospital.

The storage unit 215 stores various application programs. In various embodiments, the storage unit 215 comprises one or more memory types, such as RAM, ROM, local memory such as a cache memory and semiconductor memories, such as Electrically Erasable Programmable Read Only Memory (EEPROM). Further, the storage unit 215 is configured to store the medical data procured by the data acquisition unit 205 from multiple medical information systems 110, 115, 120 and 125.

The input unit 225 and the video display unit 210 are capable of inputting and outputting various medical data. The input unit 225 comprises a keypad, keyboard, touch pad, light pen, laser pen, microphone or other device by which a person may enter the object data and/or information requests such as requests for the medical data concerning the medical object into the medical workstation 105.

In an embodiment of the invention, the medical object can be associated with an information tag 230 for the purpose of identification as shown in FIG. 2. For example, FIG. 2 shows an information tag 230 affixed to a patient for use in identifying the patient. The information tags are typically utilized for tagging and electronically identifying articles by reading the object data stored in the information tag 230 using contact-less radio-frequency (RF) transmissions. The information tag 230 may be one of a radio frequency identifier (RFID), a barcode label and a magnetic stripe tag embedded in an adhesive tag that adheres to the medical object in a tamper resistant fashion. For simplicity, the system and/or method are described in terms of one information tag 230 associated with one medical object, although multiple information tags 230 may be associated and tracked individually and/or as a group. For example, a single medical object may receive one or more medications and/or medical devices, and/or medical procedures at one or more times.

The object data stored in the information tag 230 can be read and written to by the control unit 220. The control unit 220 is capable of a simultaneous communication with one or more information tags 230. The control unit 220 and the information tag 230 are tuned suitably so that RF energy can stimulate the information tag 230 to emit a signal representative of the object data stored therein. Such contact-less information tags 230 eliminate the need for an electrical contact or a line-of-sight path for communication with the control unit 220.

In addition to the object data stored, the information tag 230 comprises a non-erasable permanent identification number stored by the manufacturer. The permanent identification number can be utilized for identifying the medical object associated with the information tag 230. The information tag 230 may further include an overwrite protection feature whereby the object data stored therein may be protected from being overwritten or changed, thereby providing a measure of security.

A typical information tag 230 comprises an I-code chip that conforms to the ISO15693 format protocol for wireless RF identification tags. Available information tags 230 operate at RF frequencies between hundreds of kilo-Hertz (KHz) and several giga-Hertz (GHz). Typical frequencies for RF information tags 230 include 125 KHz, 13.56 MHZ, 915 MHZ and 2.45 GHz. For medication, medical devices and implements, an information tag 230 operating at 13.56 MHZ is typically used.

In a scenario where a physician advises the medical object for a medical procedure, the medical object registers for the medical procedure at a registration station 235 in the hospital information system. The medical staff operating the registration station 235 can store the object data that is the information concerning the medical object in the registration station 235.

Upon registering the medical object for the medical procedure, a message can be sent from the registration station 235 to the medical workstation 105. The data acquisition unit 205 of the medical workstation 105 can be configured to assign an object identification code to the medical object upon receiving the message.

The object identification code along with the additional information can be written to the information tag 230 by the control unit 220 of the medical workstation 105. The additional information may comprise a serial number, details of the medical object such as name, sex and age, diagnosis or sickness or condition, a procedure code for the identity of the medication, medical device, implement, medical procedure and/or treatment, a pictorial representation of the medical object indicating the site for the medical procedure, an identification of the surgeon and/or physician, date and time of the scheduled medical procedure, place of the medical procedure, a list of the medical data to be acquired from the medical information systems 110, 115, 120 and 125, a selected format for the display of the medical data, prescriptions, time of, dosage of and/or frequency of administration of the drugs and the like.

Figure 3:
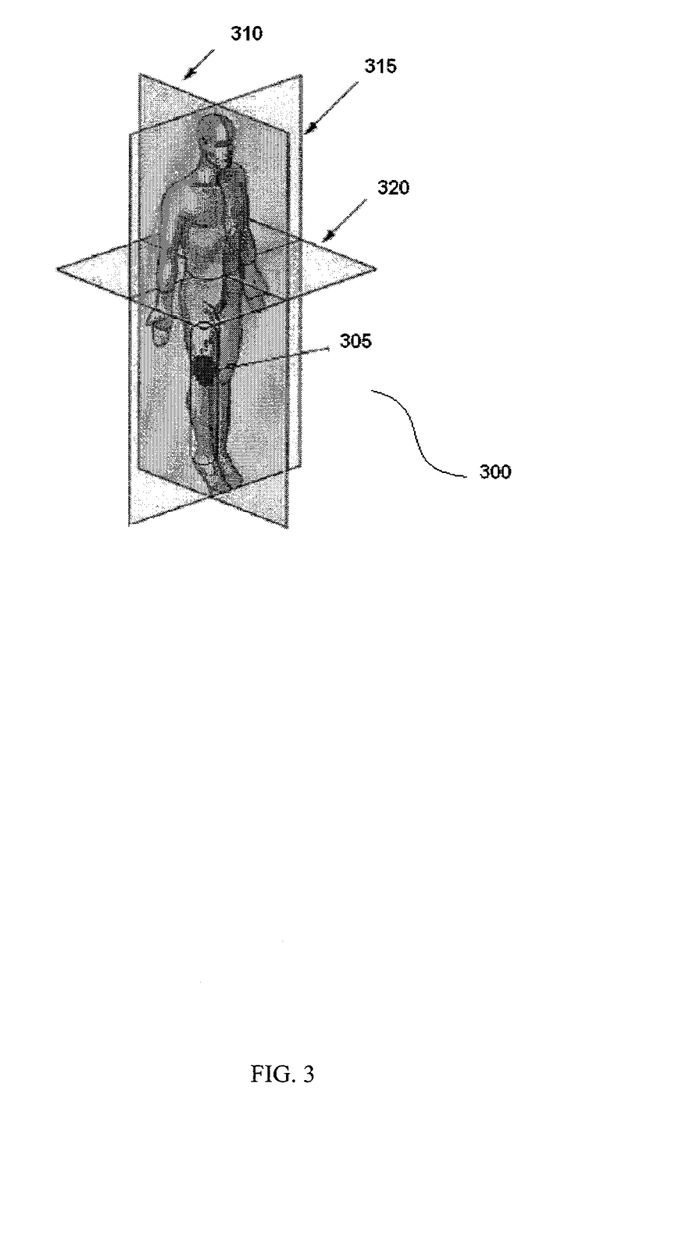
FIG. 3 shows a pictorial representation of a location of a medical procedure, in an embodiment of the invention.

In an embodiment, the information tag 230 can be configured to store an RIS identifier 300 as shown in FIG. 3. The RIS identifier 300 is a pictorial representation of the medical object indicating a location 305 of the medical procedure. The location 305 of the medical procedure can be shown with respect to a sagittal plane 310, a coronal plane 315 and a transverse plane 320. The RIS identifier 300 indicating a visual display of the location 305 of the medical procedure can help the medical staff to minimize critical medical errors such as operating on the right knee instead of the left knee. Therefore, the RIS identifier 300 provides for a simplified error check following an easy comparison of the picture with the procedure code.

By writing the object data concerning the medication and/or medical device or implement and/or medical procedure on the information tag 230, the information tag 230 may be utilized with the control unit 220 to provide, for example, warnings and reminders to the medical object, either visually or audibly, for alerting the medical object to take the medication, to have a prescription refilled or to have a medical image taken. For example: the object data stored in the information tag 230 can provide inputs for the surgical equipment list needed for the surgery. The object data from the information tag 230 can also be used to supplement medical data, which is transmitted to the data acquisition unit 205. The data acquisition unit 205 provides accounting information for the business office in order to update a personal record and a billing record of the medical object.

Upon assigning the object identification code, the data acquisition unit 205 of the medical workstation 105 can be configured to transmit the object data to at least one medical information system 110, 115, 120 and 125 coupled to the medical workstation 105. Further, the data acquisition unit 205 can be configured for a function of generating a work list and storing the generated work list in a relational database therein. The work list can be a tabulated form of multiple items, each item representing the object data concerning each medical object.

The relational database represents an aggregation of records stored in the data acquisition unit 205 (or the storage unit 215). The relational database includes, for example, a number of data fields comprising one or more of a list of the permanent identification number for each information tag 230, a list of the object identification code associated with each information tag 230, a list of the procedure code of the medical procedure associated with each information tag 230 and a list of tag coding identifiers such as the date and time for each writing of the object data to each information tag 230. The lists are comprised of aggregations of the records corresponding to each writing of the object data to each information tag 230.

Apart from the work list, a list of procedure codes can be generated for each of the medication, medical device, implement, medical procedure and/or treatment. The list can be maintained in the relational database. The access to the relational database may be controlled by access codes, passwords and the like as desired, and medical data communicated via the Internet may be encrypted, to provide the desired degree of security. Where desired, the relational database may be accessed and made available by any convenient means, e.g., by providing same on floppy disk or CD-ROM, optical CD and the like that is easily sent by mail, express mail and the like, or by making same available via communication means such as wire, cable, optical fiber, LAN, WAN, optical or radio frequency transmission, the Internet and the like.

The data acquisition unit 205 can be utilized to provide the object data on an on-line basis that is at least as current as the entry of the object data into the relational database. Each writing of the object data to the information tag 230 is replicated in the record stored in the relational database. Compiling records of the object data written to the information tags 230 in the relational database is particularly advantageous in enabling the retrieval of the object data when the information tag 230 is misplaced, lost or stolen, or if the object data stored in the information tag 230 is changed or corrupted or lost for any reason.

In response to the additional testing, medical data collection, and/or to observations made by a physician and/or other medical personnel in the course of a treatment and/or medication, the object data stored in the relational database and/or the information tag 230 may be confirmed and/or modified, including any or all of the aspects set forth above.

To ensure that the medical object is associated with the appropriate medical data, the data acquisition unit 205 can be configured to compare the procedure code with an examination code. The examination code is the code for the medical procedure as suggested by the physician. The examination code concerning the medical object can be communicated from a physician workstation 240 to the medical workstation 105 via a communication means such as wire, cable, optical fiber, LAN, WAN, optical or radio frequency transmission, the Internet and the like. Upon correlating the procedure code with the examination code, the data acquisition unit 205 can be configured to generate an indicator confirming the medical object for the suggested medical procedure.

Communication between the registration station 235, the medical workstation 105 and the physician workstation 240 may be via a communication means including but not limited to wire, cable, optical fiber, local area network (LAN), wide area network (WAN), radio (RF) transmission, optical transmission or other suitable means, or any combination thereof, with or without one or more communication hubs. Such communication may be in real time, periodic or aperiodic, and may include one or more communications, and may utilize any suitable format or protocol, such as the RS485 and/or RS232 standards.

Figure 4:
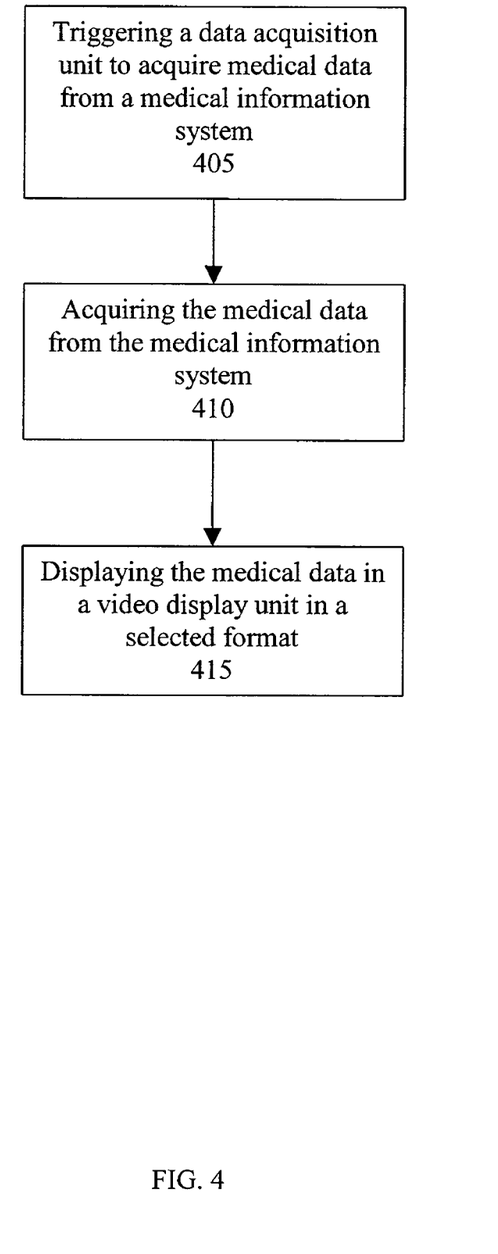
FIG. 4 shows a flow diagram of a method of automatic loading of medical data in an integrated information system, in an embodiment of the invention.

In an embodiment, the invention provides a method of automatic loading of medical data concerning a medical object in the integrated information system 100 as shown in FIG. 4. The method comprises steps of triggering the data acquisition unit 205 to acquire the medical data from one or more medical information systems 110, 115, 120 and 125 step 405, acquiring the medical data from the medical information systems 110, 115, 120 and 125 step 410, and displaying the medical data in the video display unit 210 in a selected format step 415. The triggering is based on a predetermined parameter. The predetermined parameter is at least one of a signal from the information tag 230 associated with the medical object, a predefined time interval and a threshold number of items in the work list.

In an exemplary embodiment of the invention, the trigger is generated when the medical object associated with the information tag 230 is within the communication range of the control unit 220, so as to enable the control unit 220 to receive the signal from the information tag 230.

Alternatively, the trigger can be generated upon completing a predefined time interval for example twelve hours. The data acquisition unit 205 can be configured to generate a trigger for each completion of the predefined time interval. The trigger based on the predefined time interval is advantageous when a failure of one of the medical information systems 110, 115, 120 and 125 and/or failure of the network connection between the medical workstation 105 and one of the medical information systems 110, 115, 120 and 125 occurs. For each completion of the predefined time interval, the work list can be fetched from the relational database in the data acquisition unit 205. The medical data for each of the object identification code listed in the work list can be obtained from the medical information systems 110, 115, 120 and 125.

A medical information system 110 can be termed as an unavailable medical information system 110 when the data acquisition unit 205 fails to get the medical data from the medical information system 110, for a reason such as a failure of the medical information system 110 and/or a failure of the network connection between the medical workstation 105 and the medical information system 110. The data acquisition unit 205 can further be configured to schedule a secondary trigger for fetching the medical data from one or more unavailable medical information systems. The secondary trigger can be generated based on the completion of a fraction of the predefined time interval such as one hour. The secondary trigger can be disabled upon fetching the medical data from the unavailable medical information system 110.

In yet another embodiment of the invention, the trigger is based on a threshold number of items entered in the work list. The work list comprises multiple items stored in a tabulated form. Each item indicated by a row represents the object data concerning a single medical object. For example, the work list can indicate a list of the medical objects scheduled for a medical procedure on a particular day and/or time. The data acquisition unit 205 can be configured to generate a trigger when a threshold number of items are entered in the work list. For example after the entry of every nine items in the work list the trigger can be generated. The triggering based on the number of items entered in the work list provides for a batch wise loading of the medical data. The video display unit 210 can comprise a bar gauge to indicate the completed items in the work list. Alternatively, the part of the work list for which the medical data is fetched can be deleted from the work list for the convenience.

Figure 5:
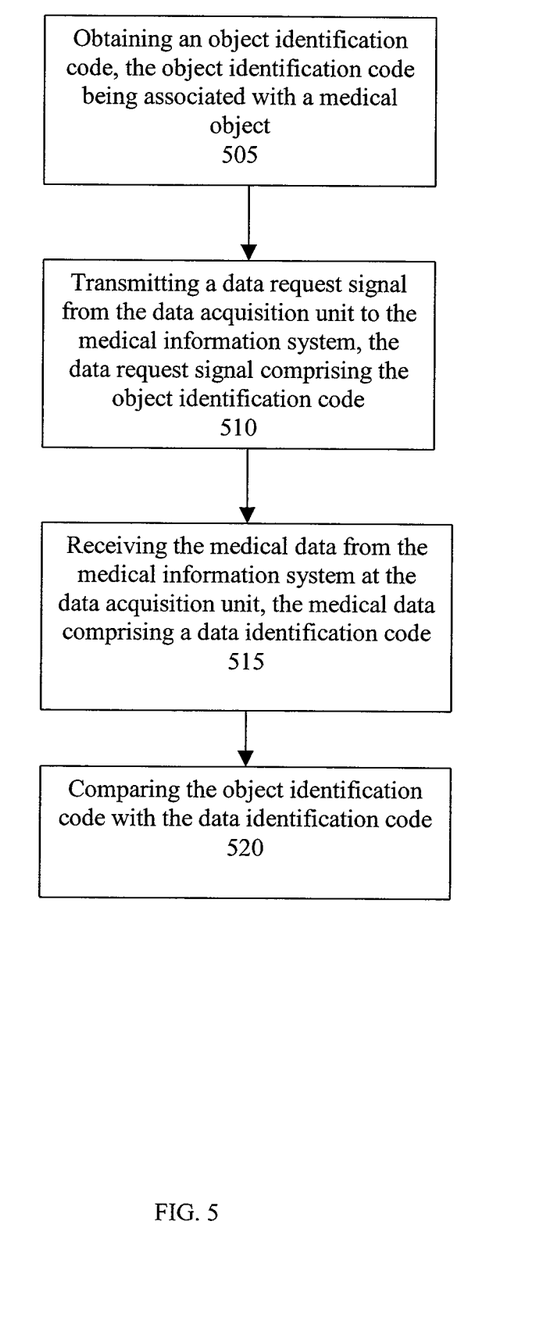
FIG. 5 shows a flow diagram of a method of acquiring medical data from a medical information system, in an embodiment of the invention.

FIG. 5 shows the method of acquiring the medical data step 410. The method comprises steps of obtaining an object identification code step 505, transmitting a data request signal comprising the object identification code from the data acquisition unit 205 to the medical information system 110 step 510 and receiving the medical data comprising a data identification code from the medical information system 110 step 515. The data identification code is an identification code for the medical data concerning the medical object. The data identification code can be representative of the object data that is stored in the medical information system 110. Although this description focuses on requesting the medical data from the medical information system 110, the medical data can also be requested from any or all of the other medical information systems 115, 120 and 125 using the same method.

It is noted that each of the permanent identification number, the object identification code, the procedure code, and the data identification code may include numerical, alphabetic, alpha-numeric and other characters and symbols, conventional or arbitrary, as may be desired.

The object identification code can be obtained from one of the work list stored in the data acquisition unit 205 and the information tag 230 associated with the medical object. When the triggering is based on the signal from the information tag, the object identification code is obtained from the information tag associated with the medical object. When the triggering is based on the predefined time interval or the threshold number of the items in the work list, the object identification code is obtained from the work list. Upon acquiring the object identification code, the data acquisition unit 205 can transmit a data request signal comprising the object identification code to multiple medical information systems 110, 115, 120 and 125. The medical data obtained from the medical information systems 110, 115, 120 and 125 comprises the data identification code.

The method 410 further comprises a step of comparing the object identification code with the data identification code step 520. An existence of a non-correlation produces the display of a warning or alarm and initiates further correlation steps. Such further steps include retrieving the records of the relational database corresponding to the particular information tag 230, for example, by the permanent identification number of the information tag 230, and displaying such retrieved records.

The matching between the object identification code and the data identification code is performed in accordance with a predetermined formula or algorithm, either on a character by character basis or on the basis of one or more combinations of the characters. Suitable formula and algorithms include, for example, parity checks or other parity representations, sum checks, field relationship checks or a predetermined relationship between the data identification code and the object identification code.

An existence of a correlation between the object identification code and data identification code authorizes the storing of the medical data in the storage unit 215. In the absence of the network connection or when a failure of one of the medical information systems 10, 115, 120 and 125 occurs, the medical data stored in the storage unit 215 can be displayed in the video display unit 210 without accessing the medical information system 110 by way of the server.

In an additional measure of preventing medical errors, the object data stored in the information tag 230 can be verified using a PDA 245. The PDA 245 is a mobile terminal allowing the medical staff such as a nurse on the move to communicate with the information tag 230 associated with the medical object. The nurse is enabled to download the work list and store the work list in the PDA 245 by accessing the relational database via the PDA 245.

The PDA 245 is configured to receive the signal from the information tag 230 available within the communication range. The medical data concerning the medical object can be fetched from at least one of the medical information systems 110, 115, 120 and 125 based on the object identification code received via the signal. The data identification code of the medical data received from each of the medical information systems 110, 115, 120 and 125 can be compared with the object identification code stored in the information tag 230. Further, the medical data concerning the medical object displayed in the video display unit 210 can be confirmed with the medical data received at the PDA 245 from multiple medical information systems 110, 115, 120 and 125.

The video display unit 210 can be configured for an automatic display of the medical data such as medical images, diagnostic reports in a selected format. A configuration corresponding to the selected format for displaying the medical data can be set by the medical staff and stored in the information tag 230. The selected format for displaying the medical data comprises information regarding the selection and arrangement of the medical data acquired from multiple medical information systems 110, 115, 120 and 125.

The control unit 220 can be configured to read the configuration stored in the information tag 230 and instruct the data acquisition unit 205 to select a display protocol corresponding to the configuration stored in the information tag 230. In the absence of the configuration the data acquisition unit 205 can be configured to pick up a default protocol.

In an exemplary embodiment of the invention, the surgeon who will conduct the medical procedure may specify the selected format. For example, when a medical procedure is to be conducted on the femur of the medical object, an image of the brain though obtained for other medical reasons is of little use to the surgeon and hence is not desired to be displayed. In addition to selection of the medical data, the surgeon would prefer the medical data to be displayed in a particular format. For example for a cardiac procedure, the surgeon may be interested in viewing the laboratory report and medical images in 1X1 mode. The provision for storing the selected format for displaying the medical data simplifies the time and effort of the medical staff in displaying the medical data as desired by the surgeon.

In yet another embodiment of the invention, a computer program product stored in a computer readable media for automatic loading of the medical data in the integrated information system 100 is provided. The computer program product comprises a routine for triggering the data acquisition unit 205 to acquire the medical data from at least one medical information system 110, 115, 120 and 125, a routine for acquiring the medical data from the medical information system 110, 115, 120 and 125 and a routine for displaying the medical data in a video display unit 210 in a selected format.

The routine for acquiring the medical data comprises a routine for obtaining an object identification code, a routine for transmitting a data request signal from the data acquisition unit 205 to the medical information system 110 and a routine for receiving the medical data from the medical information system 110 at the data acquisition unit 205. The routine for acquiring the medical data may further comprise a routine for comparing the object identification code with the data identification code of the medical data.

The computer program product can be a tangible record in one or more of a printed document, a computer floppy disk, a computer CD-ROM disk, or any other desired medium. The computer program product can be stored in a computer readable medium, such as a floppy disk or a CD-ROM disk, the medium, the computer readable files thereon may include files directing access to either a central web site or to particular web sites at which further medical data may be accessed and/or retrieved.

Some of the advantages of the method and system described in various embodiments of the invention are listed below. The invention relates generally to an improved identification system particularly designed to prevent errors in the identification of the individual medical objects in medical centers treating a large number of the medical objects. Multiple levels of error checks provided in various embodiments of the invention help in significantly reducing the medical errors.

The invention provides an integrated information system comprising a medical workstation and multiple medical information systems working together in a synchronized mode. The synchronized working of the components of the integrated information system enables an automatic loading of the medical data. The automatic loading of the medical data reduces the time consumed to procure and display the medical data as in conventional processes.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   identifying, using a processor in response to a trigger, a medical object based on an identification tag, the medical object associated with medical data;
   assigning an object identification code to the medical object based on an associated procedure;
   storing, with respect to the medical object, a pictorial representation of the medical object indicating a location of the medical procedure on the medical object with respect to a plane of reference;
associating a procedure code with the medical object;
comparing, using the processor, the procedure code with an examination code to confirm the medical object is correctly associated with the medical data and a procedure corresponding to the procedure code;
generating an indicator confirming the medical object for the procedure; and
storing the medical object and associated object identification code, pictorial representation, and procedure code in response to the indicator.

2. The method of claim 1, wherein a plurality of medical objects are identified from data acquired from a plurality of medical information systems in communication with an integrated information system.

3. The method of claim 2, wherein each medical information system comprises one of a laboratory information system (LIS), a clinical information system (CIS), a radiology information system (RIS) and a picture archival and communication system (PACS).

4. The method of claim 1, further comprising displaying the medical data in a selected format.

5. The method of claim 4, wherein the selected format is a selection and arrangement of the medical data in a format specified by a medical staff.

6. The method of claim 1, wherein the trigger comprises at least one of a signal from an information tag and a predefined time interval.

7. The method of claim 1, wherein the object identification code is obtained from at least one of a worklist and an information tag attached to the medical object.

8. The method of claim 1, wherein additional information associated with the medical object comprises a serial number, details of the medical object, diagnosis or sickness or condition, a procedure code for the identity of the medication, medical device, implant, medical procedure and/or treatment, a pictorial representation of the medical object indicating the site for the medical procedure, an identification of the surgeon and/or physician, date and time of the scheduled medical procedure, place of the medical procedure, a list of the medical data to be acquired from the medical information systems, a selected format for the display of the medical data, prescriptions, time of, dosage of and/or frequency of administration of the drugs.

9. A tangible computer readable storage device or disc including instructions for execution by a computer, the instructions, when executed, causing the computer to implement a method comprising:
identifying, in response to a trigger, a medical object based on an identification tag, the medical object associated with medical data;
assigning an object identification code to the medical object based on an associated procedure;
storing, with respect to the medical object, a pictorial representation of the medical object indicating a location of the medical procedure on the medical object with respect to a plane of reference;
associating a procedure code with the medical object;
comparing the procedure code with an examination code to confirm the medical object is correctly associated with the medical data and a procedure corresponding to the procedure code;
generating an indicator confirming the medical object for the procedure; and
storing the medical object and associated object identification code, pictorial representation, and procedure code in response to the indicator.

10. The computer readable storage medium of claim 9, wherein the method further comprises displaying the medical data in a selected format.

11. The computer readable storage medium of claim 10, wherein the selected format is a selection and arrangement of the medical data in a format specified by a medical staff.

12. The computer readable storage medium of claim 9, wherein the trigger comprises at least one of a signal from an information tag and a predefined time interval.

13. The computer readable storage medium of claim 9, wherein a plurality of medical objects are identified from data acquired from a plurality of medical information systems in communication with an integrated information system.

14. The computer readable storage medium of claim 9, wherein each medical information system comprises one of a laboratory information system (LIS), a clinical information system (CIS), a radiology information system (RIS) and a picture archival and communication system (PACS).

15. The computer readable storage medium of claim 9, wherein the object identification code is obtained from at least one of a worklist and an information tag attached to the medical object.

16. The computer readable storage medium of claim 9, wherein additional information associated with the medical object comprises a serial number, details of the medical object, diagnosis or sickness or condition, a procedure code for the identity of the medication, medical device, implant, medical procedure and/or treatment, a pictorial representation of the medical object indicating the site for the medical procedure, an identification of the surgeon and/or physician, date and time of the scheduled medical procedure, place of the medical procedure, a list of the medical data to be acquired from the medical information systems, a selected format for the display of the medical data, prescriptions, time of, dosage of and/or frequency of administration of the drugs.

17. An integrated information system comprising a processor and a memory, the processor configured to:
identify, in response to a trigger, a medical object based on an identification tag, the medical object associated with medical data;
assign an object identification code to the medical object based on an associated procedure;
store, with respect to the medical object, a pictorial representation of the medical object indicating a location of the medical procedure on the medical object with respect to a plane of reference;
associate a procedure code with the medical object;
compare the procedure code with an examination code to confirm the medical object is correctly associated with the medical data and a procedure corresponding to the procedure code;
generate an indicator confirming the medical object for the procedure; and
store the medical object and associated object identification code, pictorial representation, and procedure code in response to the indicator.

18. The system of claim 17, wherein a plurality of medical objects are identified from data acquired from a plurality of medical information systems in communication with the integrated information system.

19. The system of claim 18, wherein each medical information system comprises one of a laboratory information system (LIS), a clinical information system (CIS), a radiology information system (RIS) and a picture archival and communication system (PACS).

20. The system of claim 17, wherein the trigger comprises at least one of a signal from an information tag and a predefined time interval.

21. The system of claim 17, wherein the object identification code is obtained from at least one of a worklist and an information tag attached to the medical object.

22. The system of claim 17, further comprising displaying the medical data in a selected format.

23. The system of claim 17, wherein additional information associated with the medical object comprises a serial number, details of the medical object, diagnosis or sickness or condition, a procedure code for the identity of the medication, medical device, implant, medical procedure and/or treatment, a pictorial representation of the medical object indicating the site for the medical procedure, an identification of the surgeon and/or physician, date and time of the scheduled medical procedure, place of the medical procedure, a list of the medical data to be acquired from the medical information systems, a selected format for the display of the medical data, prescriptions, time of, dosage of and/or frequency of administration of the drugs.

\* \* \* \* \*